(12) United States Patent
Osborne et al.

(10) Patent No.: US 8,139,288 B2
(45) Date of Patent: Mar. 20, 2012

(54) PRISM DESIGN FOR SCANNING APPLICATIONS AND ILLUMINATION OF MICROSCOPY SAMPLE

(75) Inventors: Mark Osborne, Saffron Walden (GB); Jason Bryant, Saffron Walden (GB); Bojan Obradovic, Saffron Walden (GB); Harold Swerdlow, Saffron Walden (GB)

(73) Assignee: Illumina Cambridge Limited, Essex (GB)

( * ) Notice: Subject to any disclaimer, the term of this patent is extended or adjusted under 35 U.S.C. 154(b) by 335 days.

(21) Appl. No.: 12/381,154

(22) Filed: Mar. 6, 2009

(65) Prior Publication Data
US 2009/0237670 A1 Sep. 24, 2009

Related U.S. Application Data

(60) Division of application No. 10/892,821, filed on Jul. 16, 2004, now Pat. No. 7,518,764, which is a continuation-in-part of application No. PCT/GB2003/000154, filed on Jan. 15, 2003.

(51) Int. Cl.
*G02B 21/06* (2006.01)
(52) U.S. Cl. .................................... 359/385; 359/222.1
(58) Field of Classification Search ........................ None
See application file for complete search history.

(56) References Cited

U.S. PATENT DOCUMENTS

| 5,610,391 | A | 3/1997 | Ringlien |
| 5,980,831 | A | 11/1999 | Braiman et al. |
| 6,144,498 | A | 11/2000 | Bryars et al. |
| 6,175,107 | B1 | 1/2001 | Juvinall |
| 6,255,642 | B1* | 7/2001 | Cragg et al. ................. 250/216 |
| 6,327,238 | B1 | 12/2001 | Nishiwaki et al. |

FOREIGN PATENT DOCUMENTS

| JP | 100090169 A | 4/1998 |
| JP | 100090169 A | 4/1998 |

OTHER PUBLICATIONS

UK Search Report on GB 0311838.7 dated Oct. 16, 2003.
International Search Report dated Mar. 26, 2003 established by the European Patent Office International Search Authority.

* cited by examiner

*Primary Examiner* — Derek S Chapel
(74) *Attorney, Agent, or Firm* — John T. Murphy

(57) ABSTRACT

A prism for use in scanning applications such as total internal reflection microscopy in which the prism is translated relative to an incident light beam. A geometry is disclosed which cancels walk of the beam footprint at the base of the prism. Walk of the beam footprint due to irregularities in a largely planar sample surface located at the prism base are cancelled by coupling movement of the incident light beam to movement of the sample in the field of view of an objective lens, for example as part of an autofocus arrangement.

5 Claims, 7 Drawing Sheets

PRISM DESIGN FOR SCANNING APPLICATIONS AND ILLUMINATION OF MICROSCOPY SAMPLE

REFERENCE TO RELATED APPLICATIONS

The present application is a Division of application Serial No. 10/892,821, filed on Jul. 16, 2004 now U.S. Pat. No. 7,518,764, which, in turn, is a continuation-in-part of International application Ser. No. PCT/GB2003/000154 with an International filing date of Jan. 15, 2003. Applicants claim the benefits of 35 U.S.C. §120 as to the immediate parent application and to the said PCT application, and the entire disclosures of both applications are incorporated herein by reference in their entireties.

FIELD OF THE INVENTION

The present invention relates to scanning applications in which a sample, together with an angular optic such as a triangular or trapezoidal prism, are scanned in a fixed laboratory frame of reference. The fixed laboratory frame is defined by a fixed light source generating a fixed light beam and a detector. The angular optic couples the light beam to the base interface of the angular optic where the sample is located, such that the beam is incident on the base interface at an off normal angle. In such applications it is desirable that the intercept of the light beam at the base interface of the angular optic (the "footprint") remains stationary in the laboratory frame as the optic and sample are scanned so that there is no loss of image integrity at the detector.

The present invention also relates to scanning applications involving imaging systems and techniques in which an illumination beam of light is directed to a largely planar sample at an oblique angle.

BACKGROUND OF THE INVENTION

One example application is Total Internal Reflection Microscopy, which is a technique for observing samples illuminated by an evanescent wave. Total internal reflection occurs when a beam of light travelling through a very dense medium such as glass encounters an interface with a less dense medium such as air or water, at an angle to the normal which is greater than the critical angle for the interface. The critical angle for a glass/water interface is given by Fresnel's Law of Refraction as:

$$\theta_c = \sin^{-1}(n_{water}/n_{glass})$$

At angles greater than the critical angle, when total internal reflection takes place, an electric field component of the light penetrates through the interface into the water as an evanescent wave. The evanescent wave has the same wavelength as the incident beam but penetrates only a very short distance into the water, typically no more than 1 μm. The evanescent wave decays exponentially from the interface into the water with a characteristic penetration depth dependent on the wavelength and angle of incidence of the totally internally reflected light.

In Total Internal Reflection Fluorescence Microscopy, fluorophores may be excited by the light in the evanescent field if they are close to the glass/water interface, but fluorophores further away in the bulk of the solution will not be excited. The result is that images with very low background fluorescence are obtained. FIG. 1 shows a typical instrument set up used in Total Internal Reflection Fluorescence Microscopy. A sample is placed such that it is located directly on the interface of the base of a light coupling optic or dispersion prism 1. Alternatively, a glass slide 2 may be optically matched to the prism, and the sample located on the base of the slide. Total internal reflection then occurs at the base of the slide. Typically, the objective lens 3 and external light source 4 are fixed in the lab frame and the sample on which the light coupling optic or prism is fixed is scanned in a plane perpendicular to the objective lens axis. The prism 1 therefore moves relative to the objective lens 3 and the light source 4. Conventionally a 45° or 60° dispersion prism is used, but to obtain light beams incident on the base of the prism at angles close to and greater than the critical angle, the light must usually be incident on the input face of the prism at off normal angles of incidence to achieve refraction of the beam at the air/glass interface. The deviation of the beam causes the reflection footprint at the base of the prism 1 to walk db as the prism is translated dx towards or away from the light source. In a limiting case light propagating parallel to the prism base will be refracted such that the footprint at the prism base moves equally and in the same direction as the prism (db/dx=0). In this case the footprint moves dx in the lab frame and the illuminated area moves rapidly away from the imaging lens as the sample is scanned.

In imaging systems in which excitation or illumination of a sample is largely confined to a sample plane, such as in total internal reflection fluorescence microscopy (TIRFM), accurate excitation and imaging of material in this plane can be extremely sensitive to movements or irregularities of the plane. This is especially true in systems of high magnification, since a higher magnification generally results in a smaller field of view and depth of focus. If the sample is scanned, replaced or otherwise moved, adjustments need to be made to keep the image in focus. If the illumination beam is obliquely incident on the sample plane, as it is in TIRFM, irregularities or movements in the sample plane cause the intersection, or footprint of the beam in the plane to move laterally across the imaging area. This effect may be termed footprint misalignment, and results in the objective or imaging lens looking at a different part of the sample plane to that which is being illuminated.

Variations and irregularities may be present across a particular sample, causing footprint misalignment as the sample is scanned. Variations may also arise between consecutive samples, making an initial alignment of the illumination beam necessary when a new sample is loaded or set up.

Footprint misalignment has been found to be a particular problem in setting up a new sample for scanning with the TIRFM technique. In FIG. 2, the TIRFM arrangement of FIG. 1 is represented in section. An illumination laser beam 5 is transmitted through the prism 1, before passing through a layer of index matching fluid into the sample slide 2. The thickness of the slide in the drawing has been greatly exaggerated for clarity. The sample plane is defined by the lower surface of the slide. The angle of incidence of the beam onto the lower surface of the slide is sufficiently oblique that total internal refraction takes place, and none of the illumination beam propagates through the bottom of the slide 2. For a glass-water interface an angle of incidence of about 68° is generally appropriate for ensuring total internal reflection of all components of the beam.

In the unaligned arrangement shown in FIG. 2, the focal plane 10 of the objective lens 3 lies within the slide 2, and the illumination footprint 12 lies to the left of the field of view of the objective lens 3. Approximate focus of the objective on the sample 14 can be achieved by, for example, observing the geometry of a drop of immersion oil between the objective lens 3 and a cover slip placed over the sample 14, thus bringing the focal plane 10 roughly into coincidence with the sample 14. Approximate alignment of the footprint 12 with a region of interest of the sample surface being imaged using the objective lens can then be achieved by adjusting the illumination laser beam 5 and observing the scattered light until a high contrast background is observed, as long as the focus is not too far from correct. This high contrast background originates from point defects and irregularities in the surface and may be described as a grainy image, typically including bright circular rings which may consist of intermittent bright and dark rings ("airy discs") when slightly defocussed or a bright point when in focus. Finding and correctly identifying this grainy image is difficult. If the footprint 12 is too far from the objective lens field of view, which may be very small, a largely blank, or at least less grainy image will result. If a bubble is present in either the immersion oil or index matching fluid or if light reflects from the rim of the objective lens aperture 3 then the image may become swamped with scattered light.

When a grainy image has been found, the objective lens 3 is translated towards or away from the sample 14 until a scratch or point defect on the slide-sample interface comes into focus, at the same time adjusting the footprint to complete the alignment. This process is often hampered by the presence of strong scatter, and is made more difficult because the focus in a first dimension and the footprint position in the two other dimensions need to be adjusted at the same time. The process becomes particularly difficult at high magnifications and correspondingly small depths of focus and small fields of view. These set-up difficulties present significant obstacles when designing TIRFM or similar systems which are suitable for automated or semi-automated high throughput and/or scanning applications. When the sample is scanned, irregularities in the sample surface, even if compensated for using an autofocus arrangement, can still result in footprint misalignment.

OBJECTS OF THE INVENTION

It is an object of the present invention to obtain a footprint which is static in the laboratory frame of reference, defined by the objective lens and light source, such that the area illuminated at the glass/aqueous interface does not move away from the optical axis of the lens as the sample and prism are scanned.

It is also an object of the invention to address the difficulties encountered in aligning and focussing the optics in imaging systems in which a largely planar sample is illuminated at an oblique angle.

It is also an object of the invention to reduce misalignments and focussing problems when an obliquely illuminated sample is scanned.

SUMMARY OF THE INVENTION

The invention addresses the problems of the related prior art by providing a prism having particular advantageous properties, and apparatus and methods using such a prism. The invention also addresses problems of the related prior art by providing correction of an illumination footprint by adjusting an optical path synchronously with changes in the position of a sample surface or with the position of an element which moves synchronously with the sample surface, with which the prism of the invention may advantageously be combined.

In particular, the invention provides a scanning apparatus which comprises:
a light source for generating a light beam; and
an angular prism coupled to a sample at a base interface;
characterised in that the base angle $\theta_p$ of the prism satisfies the equations:

$$\frac{(\cos^2\theta_c - \sin^2\theta_p)(\tan\theta_i\sin\theta_p + \cos\theta_p)}{\cos\theta_c\cos(\theta_p \pm \theta_c)} = 1 \quad \text{(Eqn 1)}$$

and $$n_i\sin\theta_i = n_p\sin(\theta_p - \theta_c) \quad \text{(Eqn 2)}$$

wherein $\theta_c$ is the coupling angle required for light incident at the base interface of the prism, $\theta_i$ is the incident angle of the light beam on the prism, $n_i$ is the refractive index of the medium at the interface where the light beam enters the prism and $n_p$ is the refractive index of the prism.

A scanning method according to the invention comprises the steps of:
generating a light beam;
providing an angular prism in the path of the light beam, the prism being coupled to a sample at a base interface; and
moving the prism and sample relative to the light beam;
characterised in that the base angle $\theta_p$ of the prism satisfies the equations:

$$\frac{(\cos^2\theta_c - \sin^2\theta_p)(\tan\theta_i\sin\theta_p + \cos\theta_p)}{\cos\theta_c\cos(\theta_p \pm \theta_c)} = 1 \quad \text{(Eqn 1)}$$

and $$n_i\sin\theta_i = n_p\sin(\theta_p - \theta_c) \quad \text{(Eqn 2)}$$

wherein $\theta_c$ is the coupling angle required for light incident at the base interface of the prism, $\theta_i$ is the incident angle of the light beam on the prism, $n_i$ is the refractive index of the medium at the interface where the light beam enters the prism and $n_p$ is the refractive index of the prism.

It has been found that, if the prism satisfies the above criteria, a solution exists where the footprint of the light beam on the base of the prism walks in an equal and opposite direction to the prism's translation in the lab frame i.e. db=−dx. Therefore, the point where the light incident to the prism intercepts the prism base is fixed in the lab frame. This results in scanning of the sample without movement of the footprint with respect to a detector fixed in the lab frame and hence no loss of image integrity.

A solution is found wherein $\theta_p = \theta_c$ and $\theta_i = 0$.

Preferably, the apparatus comprises a total internal reflection microscopy apparatus and includes means for detecting interaction of the sample at the base of the prism or optically matched slide with an evanescent wave formed by total internal reflection of the light beam at the base of the prism or at the base of a slide which is optically matched to the prism. Preferably, the method according to the present invention includes the step of detecting interaction of a sample at the base of the prism with an evanescent wave formed by total internal reflection of the light beam at the base of the prism.

For light entering the prism from air, $n_i = 1$, and therefore $$\sin\theta_i = n_p \sin(\theta_p - \theta_c)$$

For total internal reflection to occur at the base interface $\theta_c$ must be greater than or equal to the critical angle for the interface ie $$\theta_c \geq \sin^{-1}(n_s/n_p)$$

Wherein $n_s$ is the refractive index of the sample medium.

In total internal reflection microscopy, it is preferable that the coupling angle is greater than but close to the critical angle as this maximises the penetration of the evanescent wave into the sample medium. It is generally preferable that $\theta_c$ is slightly above the critical angle because, although penetration of the evanescent wave is at a maximum at the critical angle, there will be a spread of angles within the beam and, to ensure total internal reflection of the entire beam it is preferable to have $\theta_c$ slightly above the critical angle.

This also accommodates minor variations in the refractive indices of the interfacial media.

For a quartz/water interface at the base of the prism, where $n_p=1.46$, the critical angle of the base interface is 66°. A preferred value for $\theta_c$ would be 68°. A unique solution is found wherein $\theta_i=0$, and $\theta_p=68°$.

The invention also provides apparatus for imaging a sample, comprising:

an objective lens having a focal plane and an optical axis, the lens being arranged to collect light from a region of interest defined relative to said optical axis;

an illumination director controllable to direct a beam of light along an optical path so as to illuminate the sample in the region of interest at an angle oblique to said optical axis; and an illumination director controller arranged to control the illumination director relative to the sample such that the optical path remains directed to the sample in the region of interest following replacement of the sample, or movement of the sample relative to the objective lens.

The beam of light may be directed onto the sample through a prism having a base angle as set out above, in particular when the invention is applied in the construction or use of a total internal reflection microscope.

The term "objective lens" is to be understood as covering suitable compound lens arrangements and ancillary parts of any suitable objective lens assembly including non-optical parts for mounting, focussing and otherwise controlling the lens.

The illumination beam may be directed at the sample continuously. More preferably, the beam is shuttered or otherwise turned off or blocked for some or most of the time, for example to avoid photo bleaching of the sample.

The illumination director may, for example, be a mirror suitably mounted to cause the footprint of the beam of light on the sample to track the region of interest, thereby reducing or eliminating the need to make manual adjustments to the illumination director as the sample is scanned, or otherwise moved. The region of interest may cover the whole or only a part of the field of view of the objective lens, because the apparatus may be used to image, at any instant, the whole or only a part of the sample within the field of view. Usually, the region of interest will be a central portion of the field of view, relative to the optical axis of the objective lens, and could be represented as a single point in the field of view fixed, or if required moveable, relative to the optical axis.

The illumination director controller is preferably arranged to automatically adjust the illumination director and/or the optical path synchronously with movements parallel to the optical axis of a part of the sample which is within the region of interest. This could be achieved, for example, by tracking the sample surface with a range finding device and using the output of the range finding device to drive adjustment of the illumination director.

In preferred embodiments, the illumination director controller is arranged such that the position, and preferably also the orientation of the illumination director relative to the part of the sample which is currently in the region of interest remains substantially constant.

The illumination director controller may be arranged to adjust the illumination director and/or optical path synchronously with movements of the focal plane relative to the sample such that the beam of light remains directed to the intersection of said region of interest and the focal plane of the objective lens.

Preferred embodiments comprise an autofocus arranged such that the focal plane of the objective lens tracks the part of the sample which is in the region of interest. In this way, the focal plane of the objective lens and the viewed or relevant part of the sample remain coincident such that adjusting the illumination director with respect to one gives rise to adjustment with respect to the other. Typically, the autofocus will include a z-axis drive for adjusting the position of either the sample or objective lens along the optical axis of the lens. Such drives are well known in the art.

Preferably, at least a part of the objective lens is moveable in a direction parallel to its optical axis so as to bring the part of the sample which is within the field of view or region of interest into focus. The illumination director controller may then comprise a coupling arranged to adjust the illumination director synchronously with the movement of the at least part of the objective along the optical axis.

In particular, the coupling may be a direct mechanical coupling, such as a rigid bracket or other component, or combination of linked components. If an autofocus system is employed which uses a piezoelectric transducer to focus the objective lens, or similar low power arrangement, then it may be desirable to use a lightweight bracket to avoid overloading the focussing system. Alternatively, an electrical coupling could be used, for example by driving the objective lens and illumination director with similar actuators and a common signal.

Preferably, the objective lens is positioned on a first detector side of the sample, and the illumination director is positioned on the opposing illumination side of the sample, commonly referred to as transmission mode. However, the invention is also applicable to so-called reflection mode arrangements in which the beam approaches the sample from the same side as the objective.

In preferred embodiments the apparatus is a total internal reflection fluorescence microscope, in which the illumination beam reflects from an interface adjacent to the sample.

Preferably, the illumination director is or comprises a mirror. Preferably also, the optical path of the illumination beam is incident on this mirror in a direction parallel to the optical axis of the objective lens. A fine adjust mechanism, for preliminary, manual or ad hoc adjustments, may be provided on the mounting of this mirror. Preferably, however, to avoid undue vibration and consequent motion of the beam, the fine adjust mechanism is provided on a second mirror further upstream from the sample along the beam, which may more easily be rigidly mounted. The second mirror then directs the illumination beam onto the first mirror. Other arrangements of mirrors could be used.

Alternatively, the illumination director may be provided by the termination of a light guide such as an optical fibre or fibre bundle, with optics incorporated as appropriate.

The invention also provides a method of automatically correcting the illumination footprint of the optical path of a light beam on the surface of a microscopy sample, comprising the step of adjusting the position of the optical path at the sample synchronously with changes in the position of the sample surface or the position of an element which moves synchronously with the sample surface.

Conveniently, the element which moves synchronously with the sample surface may be at least a part of an objective lens assembly arranged to form an image of the sample surface.

DETAILED DESCRIPTION OF EMBODIMENTS

Figure 1:
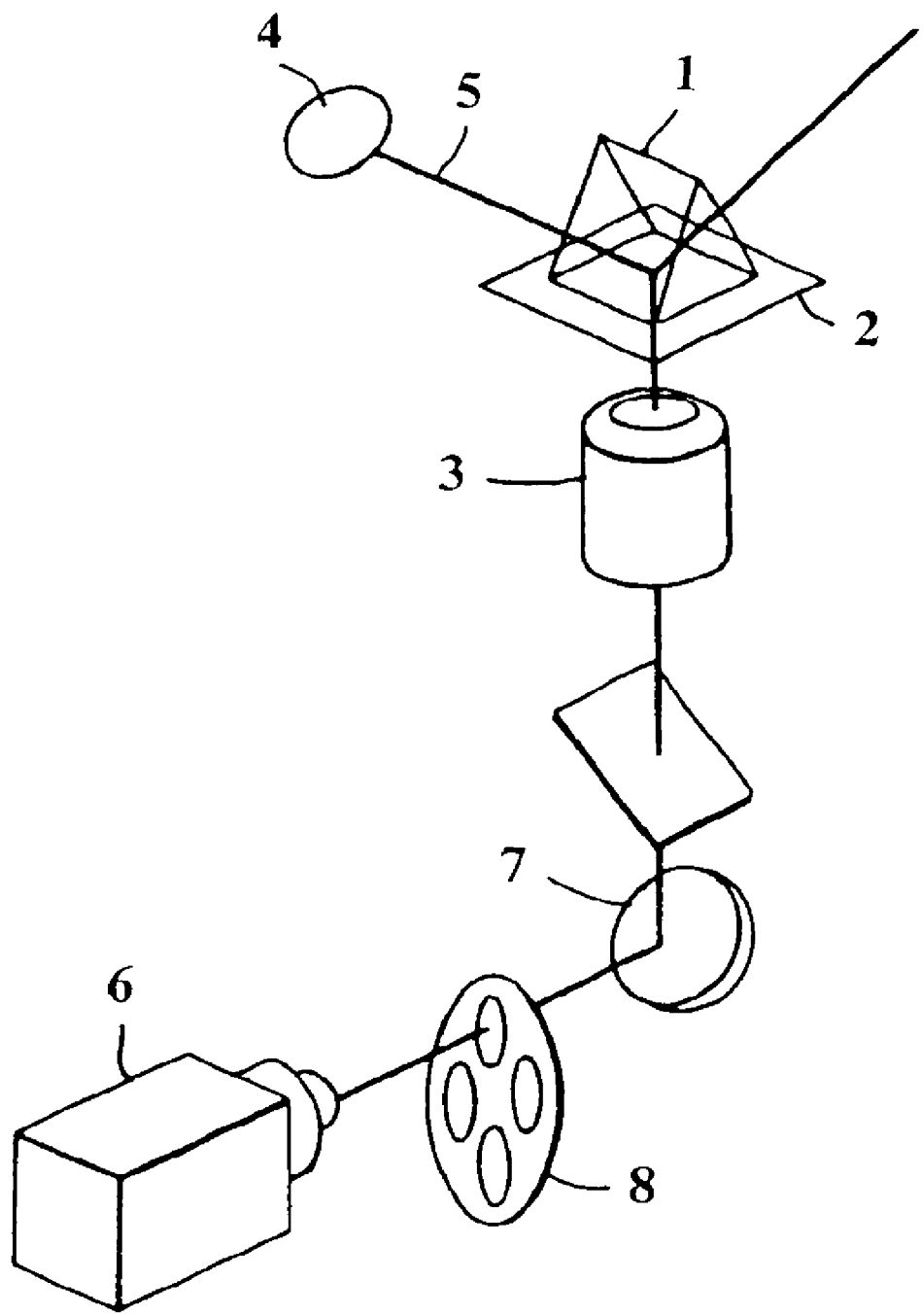
FIG. 1 shows part of an apparatus for total internal reflection microscopy.

FIG. 1 illustrates an apparatus for Total Internal Reflection Fluorescence Microscopy having a light source 4 which generates a beam 5 which is incident on a prism 1 and is totally internally reflected at the base interface of the prism. A sample is positioned adjacent to a base interface of the prism 1 and the evanescent wave interacts with the sample, producing fluorescence. The fluorescence passes through an objective lens 3 and is directed towards a CCD camera 6 by a mirror 7, passing through a filter 8.

Figure 3:
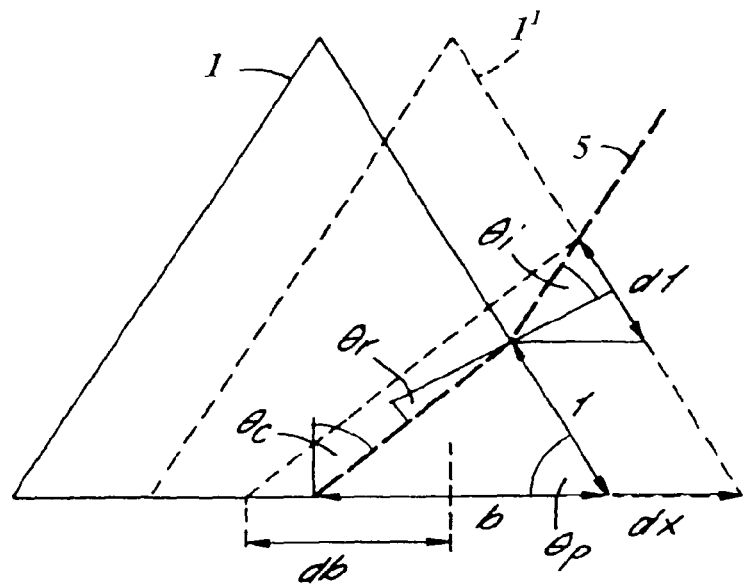
FIG. 3 is a schematic showing the total internal reflection footprint walking with the displacement of the prism.

As shown in FIG. 3, the light beam 5 is incident on the prism 1 at $\theta_i$ to the normal, is refracted as it enters the prism at $\theta_r$ to the normal and is incident on the base of the prism 1 at a coupling angle $\theta_c$, forming a footprint at the base interface. For total internal reflection to occur, $\theta_c$ must be at least the critical angle for the base interface. As the prism moves dx in the lab frame to position $1^1$, the footprint walks db in the prism frame.

The magnitude of the differential dl/db may be derived as follows:

Sine rule $\dfrac{l}{\sin(90 - \theta_c)} = \dfrac{r}{\sin\theta_p}$ or $r\cos\theta_c = l\sin\theta p$ Cosine rule $r^2 = b^2 + l^2 - 2bl\cos\theta_p$ (1) in (2) $l^2\sin^2\theta_p = \cos^2\theta_c(b^2 + l^2 - 2bl\cos\theta_p)$ quadratic in $l$ $l^2(\cos^2\theta_c - \sin^2\theta_p) - 2bl\cos\theta_p\cos^2\theta_c + b^2\cos^2\theta_c = 0$ solution to which is $$l = \frac{2b\cos\theta_p\cos^2\theta_c + \sqrt{4b^2\cos^4\theta_c\sin^2\theta_p - 4b^2\cos^2\theta_c(\cos^2\theta_c - \sin^2\theta_p)}}{2(\cos^2\theta_c - \sin^2\theta_p)}$$

expand contents of the square root $$l = \frac{2b\cos\theta_p\cos^2\theta_c + \sqrt{4b^2\cos^4\theta_c\sin^2\theta_p - 4b^2\cos^4\theta_c + 4b^2\cos^2\theta_c\sin^2\theta_p}}{2(\cos^2\theta_c - \sin^2\theta_p)}$$

take out $4b^2 \cos^2\theta_c$ common in the square root $$l = \frac{2b\cos\theta_p\cos^2\theta_c + 2b\cos\theta_c\sqrt{\cos^2\theta_c\sin^2\theta_p - \cos^2\theta_c + \sin^2\theta_p}}{2(\cos^2\theta_c - \sin^2\theta_p)}$$

factorizing gives $$l = \frac{b\cos\theta_c(\cos\theta_p\cos\theta_c + \sqrt{\cos^2\theta_c\cos^2\theta_p - \cos^2\theta_c + \sin^2\theta_p})}{\cos^2\theta_c - \sin^2\theta_p}$$

differentiating w.r.t. b $$\frac{dl}{db} = \frac{\cos\theta_c(\cos\theta_p\cos\theta_c \pm \sqrt{\cos^2\theta_c\cos^2\theta_p - \cos^2\theta_c + \sin^2\theta_p})}{\cos^2\theta_c - \sin^2\theta_p}$$

further factorization gives $$\frac{dl}{db} = \frac{\cos\theta_c(\cos\theta_p\cos\theta_c \pm \sqrt{\cos^2\theta_c(\cos^2\theta_p - 1) + \sin^2\theta_p})}{\cos^2\theta_c - \sin^2\theta_p}$$

recognising $\cos^2\theta_p - 1 = -\sin^2\theta_p$ and factorising $$\frac{dl}{db} = \frac{\cos\theta_c(\cos\theta_p\cos\theta_c \pm \sqrt{\sin^2\theta_p(1 - \cos^2\theta_c)})}{(\cos^2\theta_c - \sin^2\theta_p)}$$

recognising $1 - \cos^2\theta_c = \sin^2\theta_c$ and rooting the square $$\frac{dl}{db} = \frac{\cos\theta_c(\cos\theta_p\cos\theta_c \pm \sin\theta_p\sin\theta_c)}{(\cos^2\theta_c - \sin^2\theta_p)}$$

using trigonometric identity the differential simplifies to $$\frac{dl}{db} = \frac{\cos\theta_c\cos(\theta_p \pm \theta_c)}{(\cos^2\theta_c - \sin^2\theta_p)}$$

The magnitude of the differential dl/dx may be derived as follows:

Sine rule $\dfrac{dl}{\sin(90-\theta_p+\theta_i)} = \dfrac{dx}{\sin(180-\theta_p-(90-\theta_p+\theta_i))}$ Simplifies to $$dl\sin(90-\theta_i) = dx\,\sin(90-\theta_p+\theta_i)$$

$$dl\cos\theta_i = dx\cos(\theta_p-\theta_i)$$

$$\dfrac{dl}{dx} = \dfrac{\cos\theta_p\cos\theta_i + \sin\theta_p\sin\theta_i}{\cos\theta_i}$$

$$\dfrac{dl}{dx} = \cos\theta_p + \tan\theta_i\sin\theta_p$$

Recognising that a translation of the prism dx in the positive x direction results in a displacement db of the footprint in the negative direction and by using the chain rule $$\dfrac{-db}{dx} = \dfrac{dl}{dx} \times \dfrac{db}{dl}$$

so $$\dfrac{db}{dx} = \dfrac{-(\cos\theta_p + \tan\theta_i\sin\theta_p)\times(\cos^2\theta_c - \sin^2\theta_p)}{\cos\theta_c\cos(\theta_p\pm\theta_c)}$$

where $\theta_i = \sin^{-1}(n_p\sin(\theta_p-\theta_c))$ from Fresnel's equation, for light entering the prism from air, ($n_i=1$).

For the footprint to remain stationary in the lab frame, it must walk in an equal and opposite direction in the prism frame to the prism's translation in the lab frame, i.e. db/dx=−1.

In total internal reflection microscopy, it is preferred that the coupling angle is greater than but close to the critical angle as this maximises the penetration of the evanescent wave into the sample medium, and it is generally preferable that $\theta_c$ is slightly above the critical angle because, although penetration of the evanescent wave is at a maximum at the critical angle, there will be a spread of angles within the beam and, to ensure total internal reflection of the entire beam, it is preferable to have $\theta_c$ slightly above the critical angle.

Figure 4:
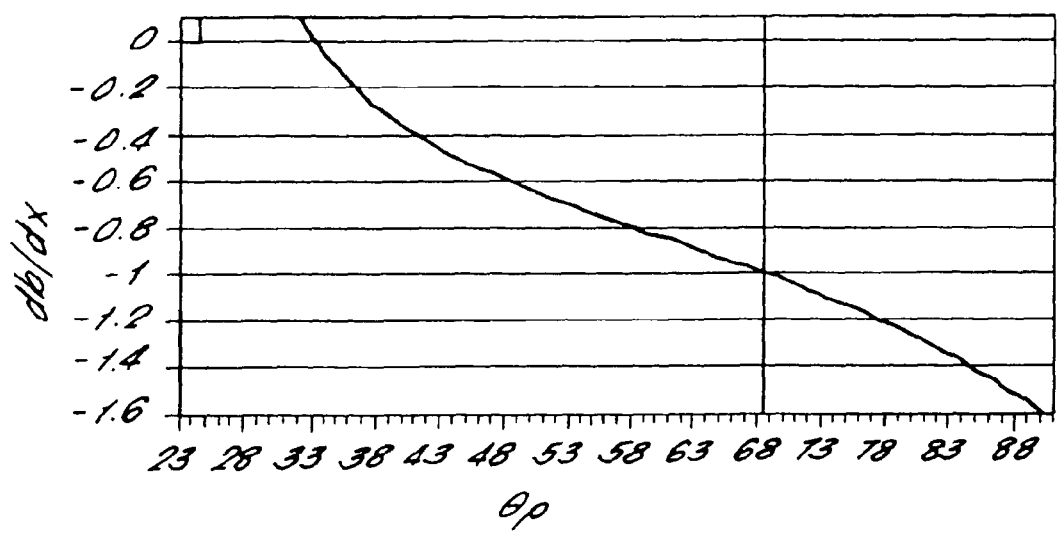
FIG. 4 is a graph of db/dx against prism angle for a quartz/water base interface and a coupling angle of 68°.

For a quartz/water interface at the base of the prism, where $n_p=1.46$, the critical angle of the base interface is 66°. A preferred value for $\theta_c$ would be 68°. FIG. 4 shows the degree of walking of the footprint with prism displacement as a function of the internal angle $\theta_p$ of the prism for $\theta_c=68°$. The prism angle required for db/dx=−1 is 68° and the light will be incident normal to the input surface of the prism, i.e. $\theta_i=0$.

Figure 5:
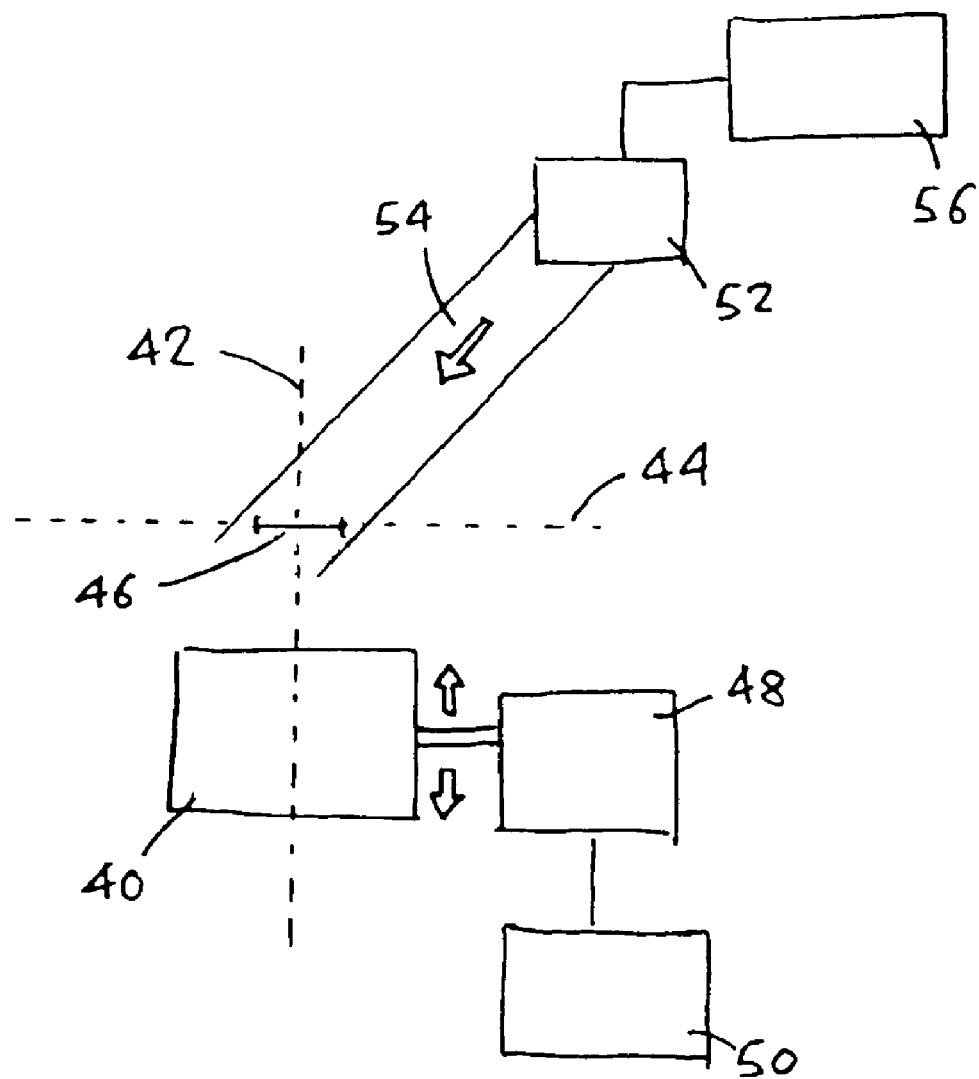
FIG. 5 shows an apparatus embodying the invention.

FIG. 5 shows a further apparatus embodying the invention which could be, for example, a total internal reflection microscope as set out above. An objective lens 40 has an optical axis 42 and a focal plane 44. A region of interest 46 of the field of view of the objective lens 40 is defined. Usually the region of interest 46 will be a fixed central region of the field of view, and is representative of the region of the field of view which is to be studied, imaged or analysed. A sample (not shown) is placed in or close to the focal plane 44 the lens and may be scanned relative to the lens 40 to enable a wider area of the sample to be studied.

A z-axis drive 48 is provided to move the lens 40 and/or sample along the optical axis 42 in order to keep the sample in focus. The z-axis drive may be controlled using autofocus logic 50, which may, for example, be responsive to a range finding mechanism output.

An illumination director 52 directs a beam of light 54 along a corresponding optical path towards the region of interest 46 within the focal plane 44, so as to illuminate the sample in the region of interest 46 at an angle oblique to the optical axis 42. Because of the oblique incident angle of the beam, relative displacement of the sample and the beam of light 54 along the optical axis 42 results in a lateral translation of the footprint of the beam of light 54 at the sample. Therefore, an illumination director controller 56 is provided to control the illumination director such that the beam of light continues to illuminate the sample in the region of interest when sample is replaced or moved relative to the objective lens 40 and/or optical path of the beam of light 54.

Figure 2:
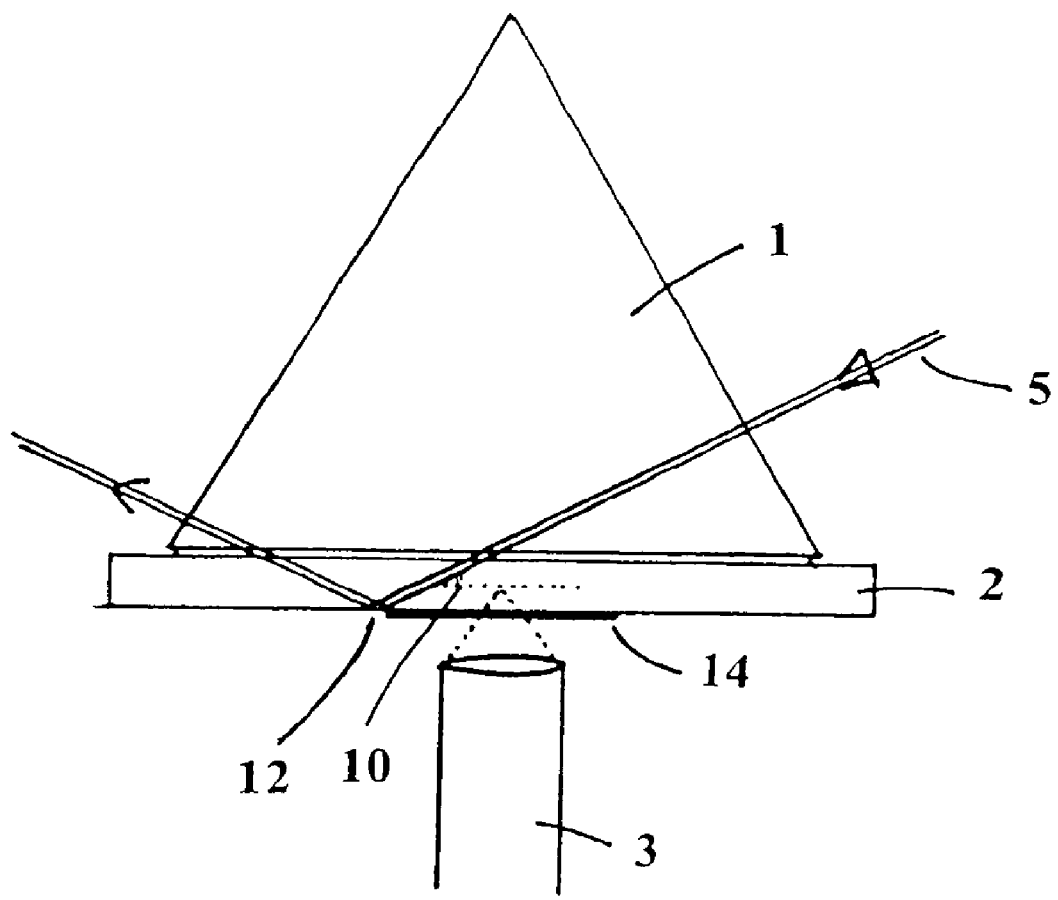
FIG. 2 illustrates the problem of achieving simultaneous objective focus and illumination beam footprint alignment in a total internal reflection fluorescence microscope.
Figure 6:
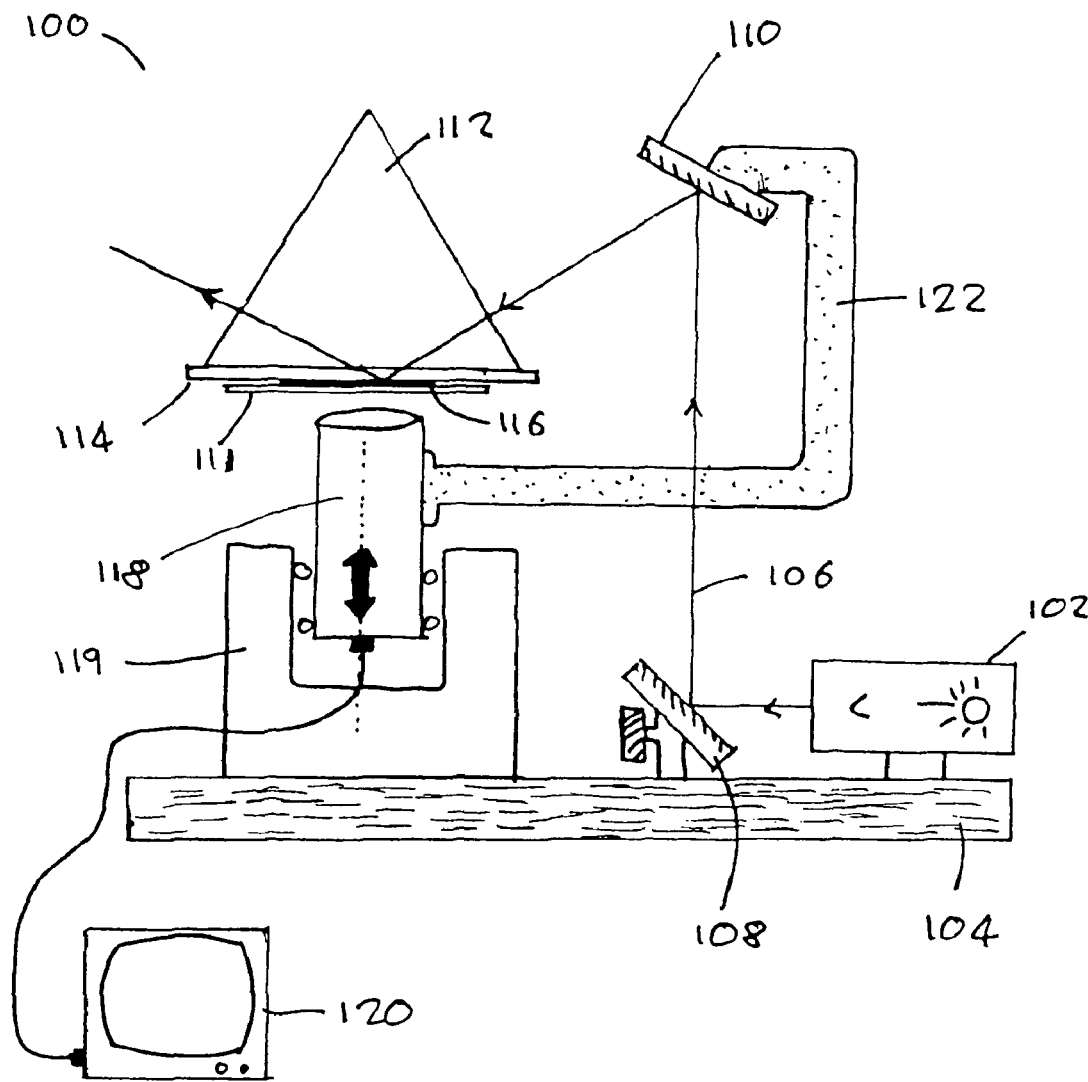
FIG. 6 shows a total internal reflection fluorescence microscope (TIRFM) embodying the invention.

Referring to FIG. 6 there is shown, schematically, a more specific arrangement 100, incorporating some of the features of FIGS. 1 and 2, for carrying out total internal reflection fluorescence microscopy, although for convenience and clarity, different reference numerals are used. A laser 102 and associated optics, mounted on a rigid optical table 104, form ar. illumination beam 106 which is directed along an optical path by reflection from a source mirror 108 and then a target mirror 110 to enter a side face of a prism 112 at an angle of incidence which is preferably approximately normal to the prism face. The source mirror is mounted on the table 104 and is provided with a manual adjustment mechanism. The target mirror is one possible embodiment of what may more generally be termed an "illumination director".

One face of a microscope slide 114 makes good optical contact with the bottom face of the prism 112, for example by means of a layer of index matching fluid. A sample 116 to be imaged forms a layer on the other face of the microscope slide. The sample will typically be immersed in an aqueous solution. A transparent cover slip 117 overlies and protects the sample 16.

The critical angle for total internal reflection at the boundary between the microscope slide 114 and the aqueous solution in which the sample 116 is immersed is typically about 64° from a normal to the surface of the slide, the precise angle depending on the values of the refractive indices of the slide and the solution. To ensure all components of the illumination beam 106 undergo total internal reflection at this boundary, and to allow for the optical effects of various solvents and temperature changes of the solvents, the target mirror 110 is arranged such that the beam is incident on this boundary at a sample angle of incidence of about 680 from the normal.

In addition to the mechanism of footprint misalignment caused by irregularities in the sample surface, illumination footprint walking can also arise if the illumination beam propagates along a longer or shorter optical path through the prism as the prism and sample are scanned. To minimise this contribution to footprint walking, the prism is preferably aligned such that the illumination beam enters the prism normal to the face of entry, and a prism having a base angle matching the desired sample angle of incidence is preferably used, as set out above. In particular, the apparatus is preferably arranged such that the prism and light beam satisfy the conditions set out in equations 1 and 2 above.

A triangular prism need not be used in embodiments of the invention, although preferred optics have the relationship between the face at which the illumination beam enters the optic and the face at which the desired total internal reflection takes place discussed above. Clearly, a variety of different optic geometries can satisfy the functional requirements, such as truncated triangular prisms and so on, and the term "prism" as used in this document should be understood to include all such optic geometries.

Although the illumination beam undergoes total internal refraction at the slide-sample boundary 114-116, an evanescent component of the beam is able to stimulate fluorescence in sample material lying within about one micrometer of the boundary. This fluorescence is collected using an objective lens 118 which forms an image of the illuminated part of the sample 116 using a CCD camera or other low light level detector. The image is displayed on monitor 120.

One or more optical filters may be located between the sample and the objective lens in order to eliminate any light from the illumination beam which may have scattered through the sample, for example off point defects in the prism or sample slide. Preferably, the filter or filters pass the maximum amount of light at the frequency of fluorescence of the sample while passing a minimum of light at the excitation frequency.

The region of the field of view of the objective lens 118 which is to be used for imaging the sample 116 may be referred to as the "region of interest". It is, of course, desirable that this region should remain within or coincident with the footprint of the illumination beam despite relative movements of the sample with respect to the objective lens and/or the target mirror 110. This region of interest may be a small or large part of the field of view of the objective lens, and may be central or offset, but will preferably be fixed relative to the optical axis of the objective lens.

Focus of the image of the sample 116, in particular within the above mentioned region of interest, is achieved by translation of the objective lens 118, or a part of the objective lens towards or away from the sample along its optical axis, which is generally perpendicular to the focal plane of the objective, using a z-axis drive 119. A bracket 122, which is preferably lightweight to avoid straining the z-axis drive 119, which may incorporate a motor or other transducer, rigidly couples the objective lens 118 to the target mirror 110, so that as the objective lens moves parallel to its optical axis the relative positions of the target mirror 110 and objective lens 118 are fixed. Additionally, the source mirror 108 is arranged such that the illumination beam 106 is incident on the target mirror 110 in a direction substantially parallel to the focussing axis or perpendicular to the objective lens focal plane and sample-slide interface. The bracket 122 is one possible embodiment of what may more generally be termed an "illumination director controller".

The sample 116 is kept in focus by means of an auto focus mechanism which causes the objective lens to move as described above, for example an auto focus mechanism as set out in copending U.K. patent application 0200844.9. The prism 112, slide 114 and sample 116 are mounted on an x-y stage (not shown) so that the sample can be scanned across the field of view of the objective lens 118, although the sample could of course be fixed and the objective moved instead along with the target mirror and other parts of the illumination optics as required.

As the sample is scanned, the objective lens generally needs to be continually refocused to adapt for irregularities, such as minor undulations, in the slide surface which cause the part of the sample within the field of view, and in particular the above mentioned region of interest, to move towards or away from the objective lens. The lightweight bracket 122 couples the focussing motions of the z-axis drive 119, under the control of the autofocus mechanism, to the target mirror 110, so that the footprint of the illumination beam 106 on the sample tracks the region of interest defined relative to the objective lens 116.

The auto focus mechanism may use a range-finding light beam directed through the objective lens 118, but offset or displaced from the central optical axis. The range-finding beam is incident on and reflects from the sample surface in or close to the region of interest, although the beam partially reflected from a surface parallel to the sample, such as cover slip 111, could possibly be used. The reflected beam re-enters the objective lens 118, again displaced from the central optical axis. Because the range-finding beam enters the objective lens off-axis, the reflected range-finding beam emerges from the objective lens laterally displaced from the incident beam. The magnitude of this displacement depends on the distance of the reflective surface, at the point of reflection, from the objective lens. The reflected beam may also emerge from the objective lens slightly aparallel to the incident beam, with the difference in beam direction also depending on the distance of the reflective surface from the lens. The displacement of the reflected beam can therefore be used to control the distance of the objective lens from the reflective surface, in an autofocus mechanism.

The displacement is preferably detected by a suitable optical detector and electrical circuitry used to control the z-axis drive 119 of the objective lens 118 accordingly. A feedback loop may be implemented by the circuitry to ensure that the objective lens remains a constant distance from the part of the sample in the region of interest.

Preferably, the incident range-finding beam entering the objective lens 118 is substantially parallel to the optical axis of the lens. Preferably, also, the incident beam entering the lens is slightly divergent or convergent so that the intensity of the beam at the reflective surface is reduced by being slightly out of focus. This reduces breakthrough of the range-finding beam, as well as photo-bleaching of the sample.

Figure 7:
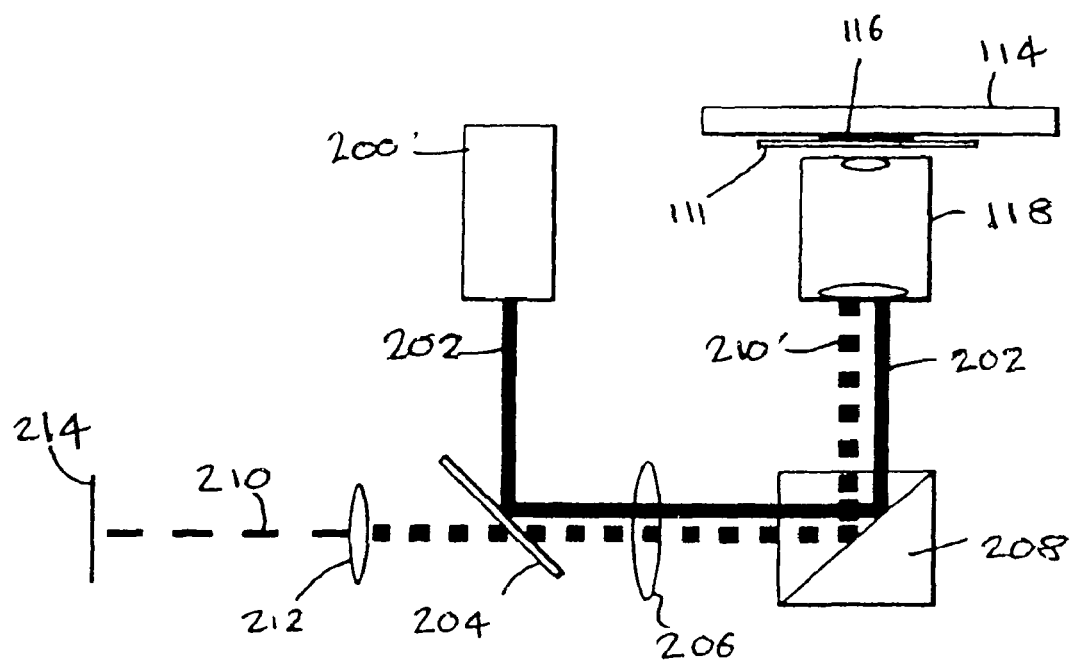
FIG. 7 shows a range finding arrangement for use with the microscope of FIG. 5 to provide an autofocus.

A particular embodiment of the above discussed autofocus mechanism is illustrated in FIG. 7. For clarity, only those components common to FIG. 6 which are required by the following discussion are shown in FIG. 7.

An autofocus laser 200 generates an incident range-finding laser beam 202 having a width of about 1 to 2 mm, which propagates towards an uncoated pellicle beamsplitter 204. The pellicle beamsplitter 204 reflects about 10% of the incident beam 202 and transmits about 90% irrespective of polarization. The transmitted light is not used.

The portion of the incident beam 202 reflected from the pellicle beamsplitter 204 is directed to a half wave plate 206 which allows the polarization of the beam to be adjusted. The half wave plate 206 must be selected as appropriate for the wavelength of the beam produced by the laser 200. The incident beam 202 emerging from the half wave plate 206 is directed to the objective lens 118 by a dichroic filter 208. The dichroic filter 208 couples the incident range-finding beam 202, having a first wavelength, into the objective lens 118, while allowing fluorescence or other image light, having a second wavelength, from the vicinity of the sample surface 116 to be transmitted to the CCD camera. In one embodiment, the objective lens is a Nikon Plan fluor, 100× magnification, NA 1.3, working distance 370 microns. This compound lens has a rear aperture of about 6 mm and a sample side aperture of about 1 mm. In such an embodiment, the incident beam 202 may have a power of about 20 µW and a diameter of about 1 to 2 mm as it enters the objective lens 118.

The incident range-finding beam is directed non-centrally or off-axis into the objective lens 118, but preferably approximately parallel to the central axis of the lens. The beam may be only slightly off center so that the central axis of the lens lies within the beam or close to the center of the beam. Alternatively, the incident beam may be more significantly off center, for example such that the beam lies outside the central axis of the lens.

The incident range-finding beam 202 is directed to the reflective surface by the objective lens 118, and is at least partially reflected to form a reflected beam 210 which is collected by the objective lens. The reflected range-finding beam 210 emerging from the objective is reflected by the dichroic filter 208, passes through the halfwave plate 206 and is incident upon the pellicle beam splitter 204. About 90% of this beam is transmitted through the pellicle beam splitter 204 and is focused using detector lens 212 onto a light sensitive element or array of elements 214.

In a preferred embodiment, the light sensitive element 214 is a quad cell located about 1 m from the reflective surface adjacent to the sample, and the detector lens 212 has a focal length of about 30 cm. The quadcell is aligned such that two of its elements are spaced apart in a direction parallel to the direction of movement of the reflected range-finding beam 210 as the reflective surface 111 moves towards or away from the objective lens 118. As a result, a change in the distance from the sample to the objective leads to a change in the relative powers of the beam portions incident on each of these two elements. The reflected range-finding beam is preferably slightly out of focus at the detector so that it impinges on a part of both elements at the same time. The remaining two elements of the quadcell are unused. Electronic circuitry coupled to the quadcell drives an activator which adjusts the position of the objective lens 118 along its optical axis 116 thus forming a feedback loop which seeks to keep the sample 116 at the focal point of the lens.

Reflections of the incident and reflected range-finding beam 202, 210 from the dichroic filter 208 and from the reflective surface 111 are polarisation dependent, governed by the Fresnel equations, so that the apparatus can be adjusted to yield a reflection beam 210 which has an optimum or maximum intensity at the light sensitive element. In particular, this can be achieved by rotating the half wave plate.

In the particular embodiment discussed above, a change in the separation of the objective lens 118 and reflective surface 111 of 1 micron results in a movement of the focused reflected range-finding beam 210 at the light sensitive element 214 of about 200 to 500 microns, depending on how far the light sensitive element 214 is from the focal point of the reflected beam 210. Preferably, the light sensitive element 214 is not placed exactly at the focal point of the reflected beam 210.

The pellicle beam splitter 204 may be replaced by a polarisation dependent optic such as a polarising beam splitter which acts such that light of a first polarisation is transmitted and light of a second polarization orthogonal to the first polarization is reflected sideways. Such a component my be used to improve the separation of the incident and reflected beams.

When a new sample 116 and slide 114 are mounted on the prism 112 and positioned within the microscope 100, the focal plane of the objective lens must be matched to the plane of the sample, and the footprint of the illumination beam 106 onto the sample must be aligned with the region of interest or field of view of the objective lens 118. Because bracket 122, or other illumination director controller couples the alignment of the optical path of the illumination beam 106 to the movement of the objective lens, and hence also to the focal plane of the objective lens, initial focussing and alignment for a new sample is much more straightforward than in the prior art.

Figure 8A:
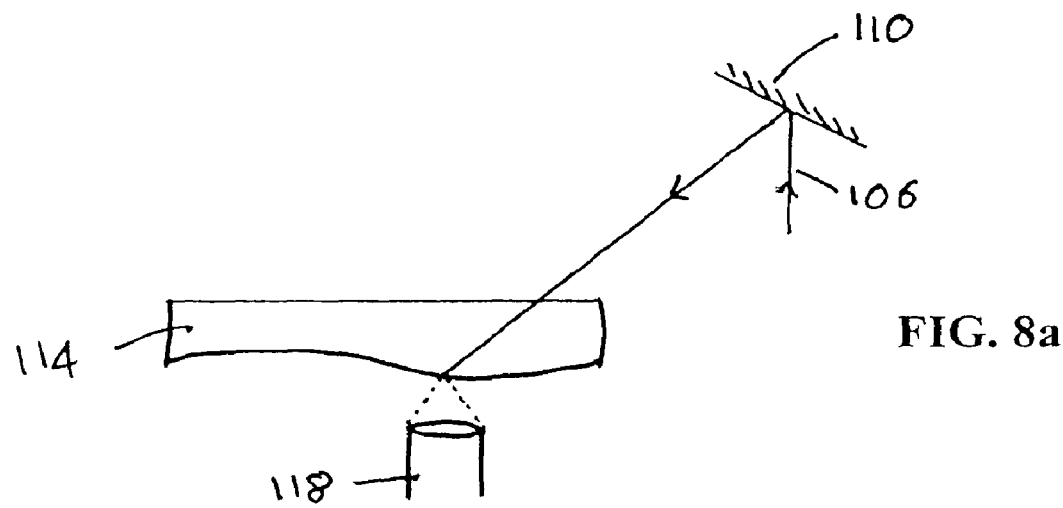
FIGS. 8a, 8b and 8c illustrate the footprint alignment method effected by the arrangement of FIG. 6.
Figure 8B:
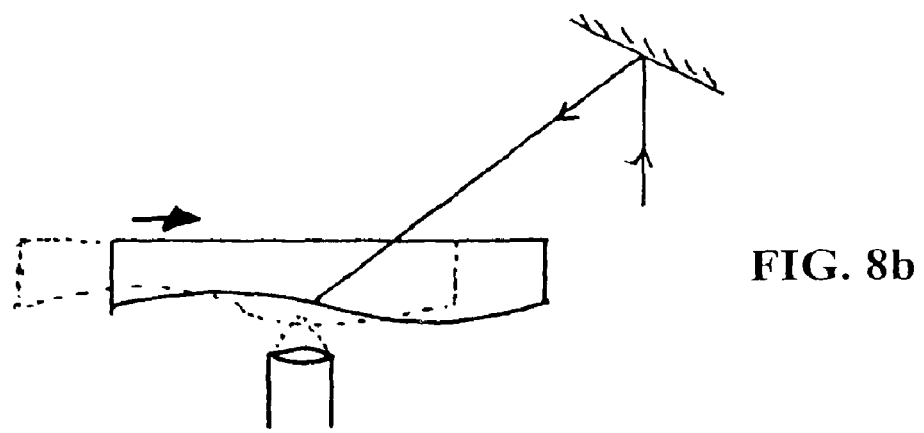
Figure 8C:
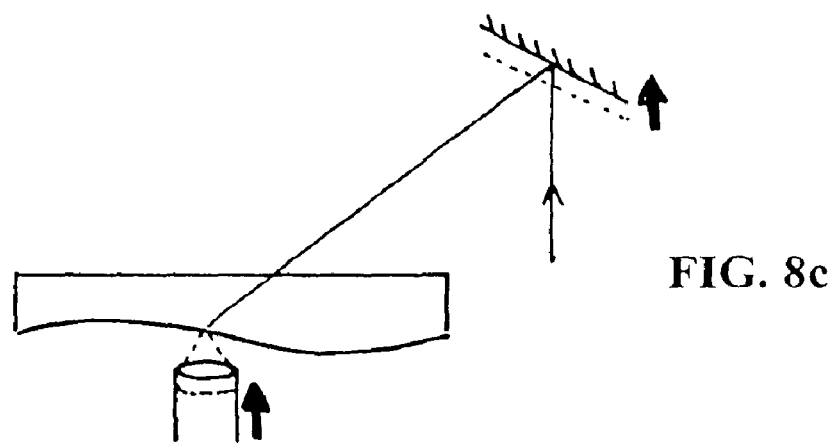

FIGS. 8a, 8b and 8c illustrate the footprint alignment method implemented by the apparatus of FIGS. 5 and 6. Each figure shows a portion of a microscope slide 114 with the vertical axis of the figures and undulations in the lower surface greatly exaggerated, and the prism 112 omitted. In FIG. 8a the focal plane of the objective lens 118 is aligned with the part of the sample plane in the region of interest. The optical path of the continuous or discontinuous illumination beam 106, which is reflected from the target mirror 110, passes through the prism (not shown) and slide 114 and is incident on the part of the slide-sample boundary coincident with the region of interest defined relative to the objective lens 118.

In FIG. 8b the slide 114 has been translated to the right, for example as part of a scanning process to image an extended area of the sample larger than the field of view. A minor undulation in the lower surface of the slide 114 has resulted in that part of the sample now within the region of interest retreating away from the objective lens focal plane. Because the optical path of the illumination beam 106 is incident at an angle oblique to the normal to the focal plane, and to the sample surface, the illumination footprint has moved to the right of the region of interest.

In FIG. 8c, an autofocus mechanism has moved the objective lens towards the slide 114 to bring the sample back into focus. Corresponding movement of the target mirror 110 has, at the same time, moved the illumination footprint back into the region of interest. In the embodiment shown in FIG. 6 the target mirror 110 is rigidly connected to the objective lens 118, so that, as illustrated in FIG. 8c, the relative positions of the target mirror 110 and the objective lens 118 remain unchanged.

Various alternatives and variations in the embodiment described above will now be discussed. Various configurations of optical components could be used in order to adjust the path of the illumination beam to control the footprint on the sample. Instead of source and target mirrors, a carefully directed optical fibre guide, or other suitable arrangement of lenses and/or mirrors could be used. Although, in the described embodiment, the optical path of the beam between the source and target mirrors is substantially parallel to the focussing axis of the objective lens, other optical path directions could be used with suitable compensating optics, for example with a prism having a different base angle.

Instead of a direct rigid coupling between the objective lens and the target mirror, the target mirror could be actuated by an actuator providing the same motion as the objective lens focussing, or z-axis actuator, with appropriate electrical coupling or common driving circuitry.

In an alternative embodiment, the target mirror or other illumination beam director element is driven according to the relative movement of the sample surface, for example in direct response to the output of a range finder which could also control the focus of the objective lens. Such a configuration could be particularly attractive if no suitable attachment to the objective lens is available, if vibration or engineering constraints make the use of a direct coupling between the objective lens and the target mirror impractical, or if no useable part of the objective lens moves in fixed spatial relationship with the objective lens focal plane.

The invention is not limited in use to TIRFM applications, or even to applications in which the illumination beam is incident from the back of the sample plane with respect to the objective lens.

The invention may be applied to the oblique illumination of a sample surface in reflection mode, or in transmission modes not requiring total internal reflection.

The invention claimed is:

1. A method for controlling the movement of a light beam in a scanning apparatus, as a function of variation in the length of the optical path of said beam, comprising
   (a) directing said light beam to an angular prism, wherein said angular prism is coupled to a sample at a base interface;
   characterised in that the base angle $\theta_p$ of the prism satisfies the equations:

$$\frac{(\cos^2\theta_c - \sin^2\theta_p)(\tan\theta_i\sin\theta_p + \cos\theta_p)}{\cos\theta_c\cos(\theta_p \pm \theta_c)} = 1$$

and $$n_i\sin\theta_i = n_p\sin(\theta_p - \theta_c)$$

wherein $\theta_c$ is the coupling angle required for light incident at base interface of the prism, $\theta_i$ is the incident angle of the light beam on the prism, $n_i$ is the refractive index of the medium at the interface where the light beam enters the prism and $n_p$ is the refractive index of the prism; and (b) moving the prism and sample relative to the light beam, wherein said variation in the length of said optical path of said light beam is controlled by aligning the prism so that said light beam enters said prism normal to the face of entry thereinto, and wherein said light beam and said prism satisfy said equations.

2. The method according to claim 1, wherein $\theta_p = \theta_c$ and $\theta_i = 0$.

3. The method according to claim 1, wherein said apparatus is a total internal reflection microscopy apparatus and includes means for detecting interaction of the sample at the base of the prism with an evanescent wave formed by total internal reflection of the light beam at the base of the prism.

4. The method according to claim 3, wherein $\theta_c \geq \sin^{-1}(n_s/n_p)$ and wherein $n_s$ is the refractive index of the sample medium.

5. The method according to claim 1, wherein said method comprises a method of total internal reflection microscopy, and further comprises the step of detecting interaction of a sample at the base of the prism with an evanescent wave formed by total internal reflection of the light beam at the base of the prism.

* * * * *